(12) United States Patent
Wong

(10) Patent No.: US 9,352,141 B2
(45) Date of Patent: May 31, 2016

(54) DOUBLE-LOCK STERILE ENTRY INTRAVENOUS PORT AND SYRINGE SYSTEM

(71) Applicant: Elizabeth Wong, Palm Springs, CA (US)

(72) Inventor: Elizabeth Wong, Palm Springs, CA (US)

( * ) Notice: Subject to any disclaimer, the term of this patent is extended or adjusted under 35 U.S.C. 154(b) by 217 days.

(21) Appl. No.: 13/763,551

(22) Filed: Feb. 8, 2013

(65) Prior Publication Data

US 2014/0228809 A1      Aug. 14, 2014

(51) Int. Cl.
| A61M 39/18 | (2006.01) |
| A61M 39/02 | (2006.01) |
| A61M 39/16 | (2006.01) |
| A61M 39/20 | (2006.01) |

(52) U.S. Cl.
CPC ............ *A61M 39/18* (2013.01); *A61M 39/0247* (2013.01); *A61M 39/165* (2013.01); *A61M 39/20* (2013.01); *A61M 2039/0205* (2013.01); *A61M 2039/0276* (2013.01); *A61M 2039/0288* (2013.01)

(58) Field of Classification Search
CPC .............. A61M 39/20; A61M 39/165; A61M 2039/205; A61M 39/18; A61M 39/0247; A61M 2039/0276; A61M 2039/0288; A61M 2039/0205
USPC ................ 604/513, 539, 256, 167.02, 167.01
See application file for complete search history.

(56) References Cited

U.S. PATENT DOCUMENTS

| 4,610,667 | A | 9/1986 | Pedicano et al. |
| 4,611,785 | A | 9/1986 | Steer |
| 5,338,307 | A | 8/1994 | Stephens et al. |
| 5,385,372 | A * | 1/1995 | Utterberg .............. A61M 39/20 215/306 |
| 5,496,288 | A | 3/1996 | Sweeney |
| 5,607,397 | A | 3/1997 | Stephens et al. |
| 5,817,067 | A | 10/1998 | Tsukada |
| 5,881,774 | A | 3/1999 | Utterberg |
| 6,003,556 | A | 12/1999 | Brugger et al. |
| 7,322,964 | B2 | 1/2008 | Pajunk et al. |
| 2004/0243059 | A1* | 12/2004 | Pajunk et al. ............ 604/164.01 |

(Continued)

FOREIGN PATENT DOCUMENTS

WO    WO2012/170813 A1    12/2012

OTHER PUBLICATIONS

Search Report and Written Opinion of International Application No. PCT/US2014/010921, issued May 1, 2014.

*Primary Examiner* — Nathan R Price
*Assistant Examiner* — Anh Bui
(74) *Attorney, Agent, or Firm* — Koppel, Patrick, Heybl & Philpott; Michael J. Ram

(57) ABSTRACT

Patients continue to acquire infections from healthcare facilities such as hospitals at an alarming rate. These infections can be transmitted when drugs or other medical materials are delivered from a syringe system into an IV line through an IV port. Some current methods of preventing contamination include swabbing the syringe with alcohol or using disposable alcohol caps; however, these methods are often inefficient. A system is described using caps that cover the entry and exit points of the IV port and the syringe system, respectively. The caps can be temporarily displaced from the entry and exit points when a sufficient force is applied to an area far enough away from the entry and exit points so as to prevent contamination. Once the caps are displaced, the syringe system can interact with the IV port using a locking mechanism such as luer locks to ensure the stability of the connection.

8 Claims, 5 Drawing Sheets

(56) References Cited

U.S. PATENT DOCUMENTS

| | | | |
|---|---|---|---|
| 2006/0206095 A1* | 9/2006 | Chu et al. | 604/539 |
| 2010/0298783 A1 | 11/2010 | Chang | |
| 2012/0016318 A1* | 1/2012 | Hoang et al. | 604/288.01 |
| 2012/0238965 A1 | 9/2012 | Chang | |

* cited by examiner

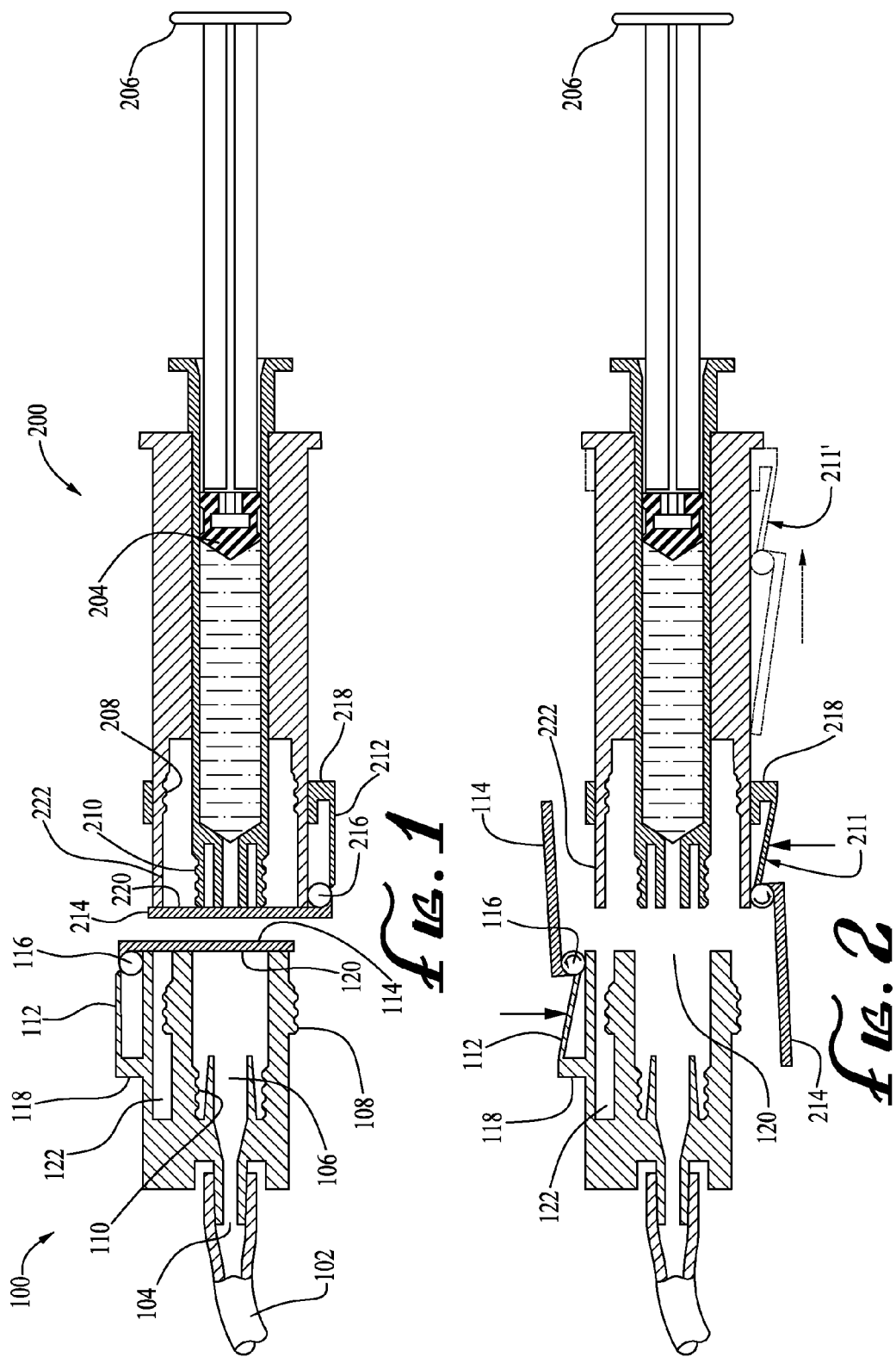

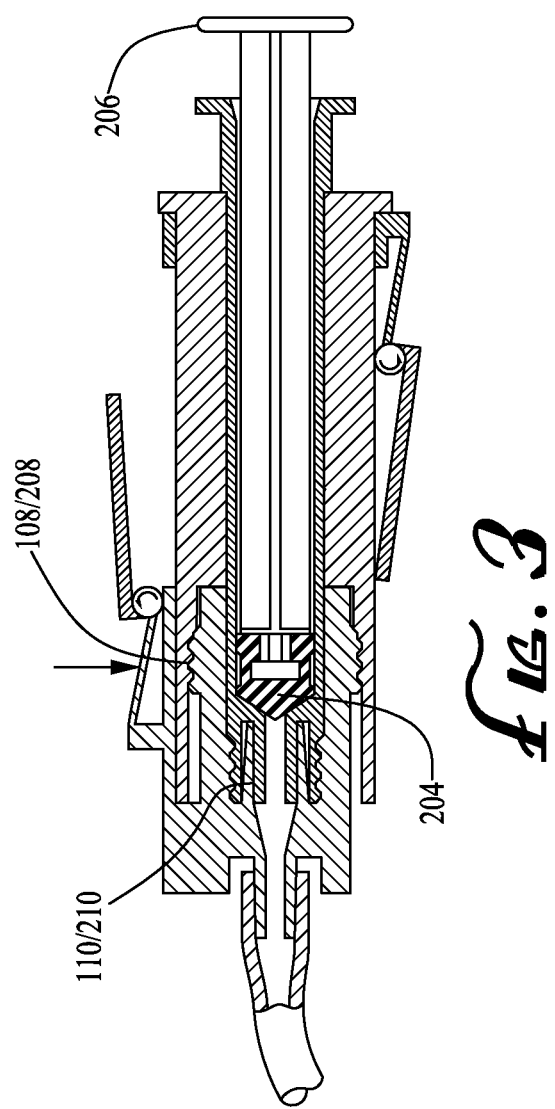

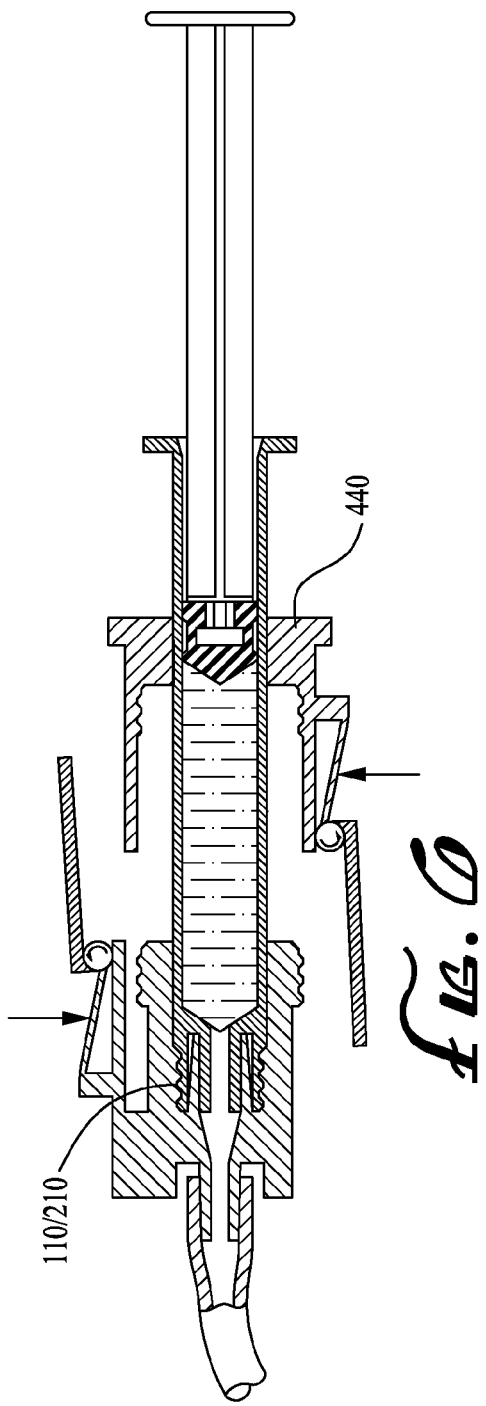
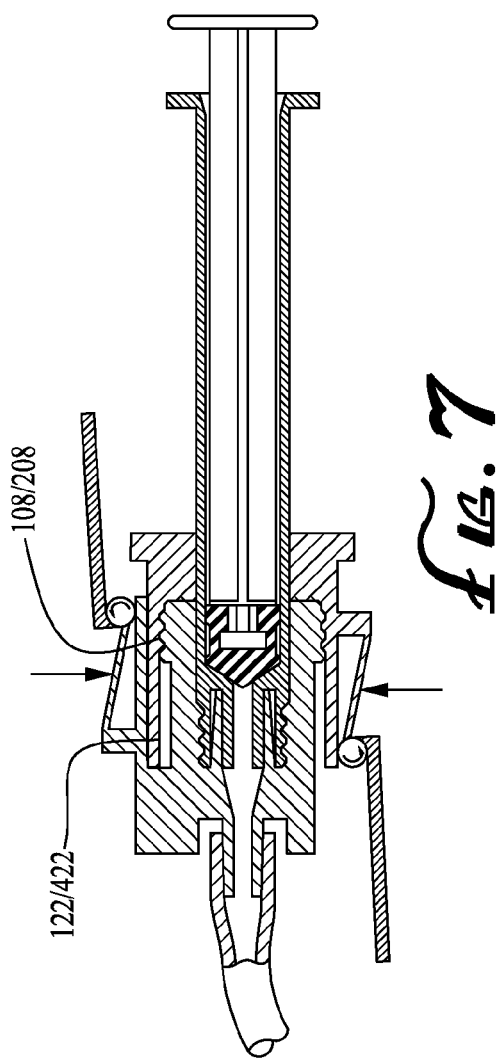

DOUBLE-LOCK STERILE ENTRY INTRAVENOUS PORT AND SYRINGE SYSTEM

The present invention is generally directed to a system comprising a sterile entry IV port and a sterile entry syringe delivery mechanism. The IV port and syringe delivery mechanism can each have a cover over their respective entry or exit point. These covers keep the components of the IV port and/or syringe delivery mechanism sterile. The IV port and/or syringe delivery mechanism covers can each include a mechanism, such as a push mechanism, placed adjacent to the entry or exit point. When sufficient force is applied to this mechanism, the cover is raised away from the entry or exit point, allowing an IV port and syringe delivery mechanism to be joined using, for example, a single or double luer lock system. By enabling the cover to be raised without touching the entry or exit points, embodiments of the present invention can prevent contamination of the IV port and syringe delivery mechanism. Further, the covers and/or the system comprising the covers can be reusable.

BACKGROUND

According to The Joint Commission, a hospital accrediting organization, patients continue to acquire healthcare-associated infections at an alarming rate. The Commission has therefore established a list of National Patient Safety Goals ("NPSG's") to combat these infections. NPSG #7 for 2011-2012 specifically addressed sterile environments and the prevention of healthcare-associated infections:

NPSG #7.01.01: Comply with either the current Centers for Disease Control and Prevention (CDC) hand hygiene guidelines or the current World Health Organization (WHO) hand hygiene guidelines.

NPSG #7.03.01: Implement evidence-based practices to prevent health care-associated infections due to multi-drug-resistant organisms in acute care hospitals.

NPSG #7.04.01: Implement evidence-based practices to prevent central line-associated bloodstream infections.

Current clinical practice generally provides for the delivery of sterile solutions (e.g. drugs, fluids, and/or blood) via uncapped luer lock syringes into uncovered luer lock needleless IV ports. In order to ensure a sterile environment, practitioners currently either swab the needleless IV port with alcohol or use single-use alcohol impregnated caps that are placed on the needleless IV port for about three minutes before delivery. As evidenced by The Joint Commission's finding that patients continue to acquire healthcare-associated infections at an alarming rate, these measures are not always effective in ensuring a sterile environment.

Various systems have been designed to aid medical professionals in the intravenous delivery of sterile solutions. Such systems are described, for example, in U.S. Pat. No. 6,003,556 to Brugger et al.; U.S. Pat. No. 5,881,774 to Utterberg ; and U.S. Pat. No. 5,817,067 to Tsukada; as well as U.S. Pat. Pub. Nos. 2012/0238965 and 2100/0298783 to Chang, the figures and descriptions of all five of these patents and publications being incorporated herein in their entirety by reference. However, these systems are lacking in many regards. For instance, none of these systems ensures a sterile environment, and extra precautions such as those described above must therefore accompany their use.

SUMMARY

Systems and methods are described for a single or double-lock sterile entry intravenous port and syringe system. The system can include caps which can be hinged. These caps can cover the entry points of the IV port and/or syringe and can prevent the contamination of these areas. In some embodiments, when ready for use a portion of each cap can be removed from the port by pressing on a mechanism spaced sufficiently away to prevent contamination by finger contact with the port opening. In turn, pressing on the mechanism causes the cap cover to raise, allowing access to the entry point of the IV port and/or syringe delivery mechanism. The system can be reusable.

BRIEF DESCRIPTION OF THE DRAWINGS

FIG. 1 shows a cut-away view of one embodiment of a sterile entry IV port adjacent one embodiment of a sterile entry syringe delivery mechanism.

FIG. 2 shows a cut-away view of the sterile entry IV port and sterile entry syringe delivery mechanism of FIG. 1 with the respective cover caps removed from the respective entry and exit points.

FIG. 3 shows a cut-away view of the sterile entry IV port and sterile entry syringe delivery mechanism of FIG. 1 in the locked (interconnected) position.

FIG. 6 shows a cut-away view of the sterile entry IV port and the sterile entry syringe delivery mechanism of FIG. 4 in a first locked position.

FIG. 7 shows a cut-away view of the sterile entry IV port and the sterile entry syringe delivery mechanism of FIG. 4 in a second locked position.

DETAILED DESCRIPTION

The present invention provides embodiments of a sterile entry IV port and a sterile entry syringe delivery mechanism that can joined together as part of a fluid delivery system. Embodiments of sterile entry IV ports and sterile entry syringe delivery mechanisms can include a cover over the entry or exit point of the IV port and the syringe delivery mechanism such that the entry/exit point and all of the components behind the entry/exit point remain sterile. This cover can be cantilevered. The movement of the covers can be caused by the application of force to a portion of the cover structure at a point spaced from the entry/exit point in order to avoid contamination of the entry/exit point. Thus, the necessity of swabbing or otherwise sterilizing the entry/exit point can be eliminated. In some embodiments the cover and movement system are reusable.

It is understood that when an element is referred to as being "on" another element, it can be directly on the other element or intervening elements may also be present. Furthermore, relative terms such as "inner", "outer", "upper", "above", "lower", "beneath", and "below", and similar terms, may be used herein to describe a relationship of one element to another. Terms such as "higher", "lower", "wider", "narrower", and similar terms, may be used herein to describe relative relationships. It is understood that these terms are intended to encompass different locations and orientations in addition to the orientation depicted in the figures.

Although the terms first, second, etc., may be used herein to describe various elements, components, regions and/or sections, these elements, components, regions, and/or sections should not be limited by these terms. These terms are only used to distinguish one element, component, region, or section from another. Thus, unless expressly stated otherwise, a first element, component, region, or section discussed below could be termed a second element, component, region, or section without departing from the teachings of the present invention.

Embodiments of the invention are described herein with reference to illustrations that are schematic illustrations. As such, the actual thickness of elements can be different, and variations from the shapes of the illustrations as a result, for example, of manufacturing techniques and/or tolerances are expected. Thus, the elements illustrated in the figures are schematic in nature and their shapes are not intended to illustrate the precise shape of a region of a package and are not intended to limit the scope of the invention.

Figure 8:
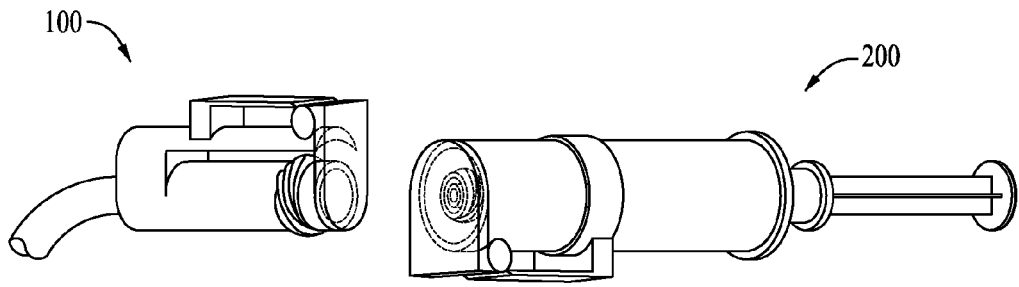
FIG. 8 is a perspective side view of the first embodiment as shown in FIG. 1.

FIG. 1 shows a cut-away view and FIG. 8 shows a side perspective view an embodiment of a sterile entry IV port 100 incorporating features of the invention (referred to below as the "FIG. 1" embodiment and/or position). An IV tube 102 is attached to the IV port 100 to receive fluid flow and is accessed through an entry point 104. A syringe 200 can be attached to the IV port 100 by placement through the IV port entry point 120. As previously described, in many current IV port/syringe systems, practitioners must either swab an IV port with alcohol, or must use single-use alcohol impregnated caps placed on the port for several minutes before injection. These systems can be tedious and in some cases ineffective. In the embodiment of FIG. 1, the port entry point 120 is instead covered by an entry cover 114. The entry cover 114, when in its closed position as shown in FIG. 1, can keep the port entry point 120 sterile such that no alcohol swabbing or impregnated caps are necessary to sterilize the device. Although not necessary, the entry cover 114 can include sterilization components such as alcohol. The entry cover 114 can be reusable or can be designed for a single use.

In order to keep the port entry point 120 sterile, it is desirable to keep practitioner body parts, such as fingers, away from the surface of the entry point 120. This can present a challenge when the practitioner must remove the prior available entry covers. The FIGS. 1 and 8 embodiment of the sterile entry IV port 100 includes a push-surface mechanism 112 such that the practitioner need not come close to contacting the sterile entry IV port 100 near the entry point 120. The entry cover 114 can be rotated about hinge 116 if a sufficient downward force is applied to push-surface 112, located between the front hinge 116 and a rear hinge or retention point 118 space longitudinally from the front hinge 116 and the entry port 120. A practitioner can apply this force without contacting the sterile entry liquid containing IV port 100 near the entry point 120.

FIG. 1 also shows an embodiment of a sterile entry syringe mechanism 200. The FIG. 1 embodiment can be used in conjunction with the FIG. 1 sterile entry IV port 100, or could be used with other IV ports. The sterile entry syringe system 200 can include an entry cover 214 and an exit point 220. As with the IV port, it is desirable to keep the exit point 220, and the components behind the exit point 220, sterile. The FIG. 1 embodiment uses a push-surface 212 similar to that of the sterile entry IV port 100. When a sufficient force is applied to push-surface 212, the entry cover 214 can rotate about a hinge 216.

Figure 9:
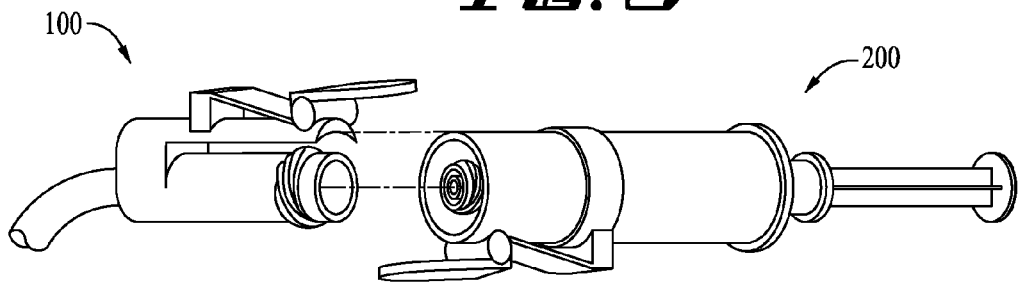
FIG. 9 is a perspective side view of the first embodiment as shown in FIG. 2.

FIG. 2 shows a cut-away view and FIG. 9 shows a side perspective view of the sterile entry IV port 100 and the sterile entry syringe mechanism 200 with their respective covers 114, 214 in an open position (referred to below as the "FIG. 2" embodiment and/or position). When a practitioner applies a sufficient downward force to the surfaces 112, 212, the surfaces move to the open positions as shown in FIG. 2; in some embodiments this is achieved by rotation about the hinges 116, 216 or retention points 118, 218, respectively. The hinges can also rotate to the positions shown in FIG. 2. Finally, the covers can open to the positions shown in FIG. 2. While in the FIG. 2 embodiment these positions are approximately 90° from the closed position, other embodiments can have entry covers 114, 214 that rotate past 90°. In some embodiments the cover cap assembly 211 can also slide back to an alternate location 211' as represented by the dotted lines in FIG. 2.

The embodiments shown in FIGS. 1 and 2 include the hinges 116, 216 and the retention points 118, 218 spaced longitudinally from the hinges 116, 216. Other embodiments can also only include one hinge or 2 or more hinges. In some embodiments hinges can replace retention points. Some embodiments do not use hinges but other mechanical devices to provide a movement to the entry covers 114, 214. In some embodiments, the entry covers 114, 214 are not rotated away from the entry point 120 and exit point 220 respectively, but instead slide away or are displaced in another manner. In some embodiments, a push-surface is not used; instead, a sliding mechanism can be used to cause the entry covers 114, 214 to be moved away from the entry point 120 and the exit point 220 respectively.

The embodiments of FIGS. 1 and 2 also include locking mechanisms to ensure that the connection between the IV port 100 and the syringe system 200 is secure. A male luer lock fitting 108 and female luer lock fitting 110 can be used in conjunction with a female luer lock fitting 208 and male luer lock fitting 210, respectively. While the FIGS. 1 and 2 embodiments include luer lock components, many other locking mechanisms such as threaded connections can also be used. Further, any combination of male/female parts is possible so long as male parts lock with compatible female parts. Finally, while the embodiments of FIGS. 1 and 2 show a double-lock system with a double-lock IV port and a double-lock syringe system, any locking system with at least one lock can be used, or a system with another securing mechanism can be used. The current application is not limited to any single securing mechanism, as such mechanisms are well known in the art.

FIG. 3 shows the sterile entry IV port 100 and the sterile entry syringe delivery mechanism 200 in their locked positions after delivery of the liquid in the syringe. First, the covers 114, 214 are displaced by pushing the surfaces 112, 212 and the IV port 100 is connected to the syringe system 200 by sliding the syringe mechanism 200 into the IV port 100. This can be made possible by including a channel 122 in the IV port to accommodate the outer wall portion 222 of the syringe mechanism. Once the syringe mechanism 200 is slid into the IV port 100, the combinations of the luer locks 108/208, 110/210 can be made simultaneously and the connection can be secured. Finally, the syringe plunger 206 is moved forward to the position shown in FIG. 3, causing the plunger lead 204 to move to the position shown in FIG. 3 for delivery of the fluid. The medical fluid is thus delivered to the IV tube 102 through the IV entry point 104 by the syringe delivery portion 204.

FIGS. 4-7 and 10-11 show variations of the embodiments shown in FIGS. 1-3 and 8-9; elements present in the earlier embodiments are identified by the same number. Whereas in the embodiments shown by FIGS. 1-3 the two sets of luer locks could be locked simultaneously, in the embodiments of FIGS. 4-7 the luer locks can lock independently.

Figure 4:
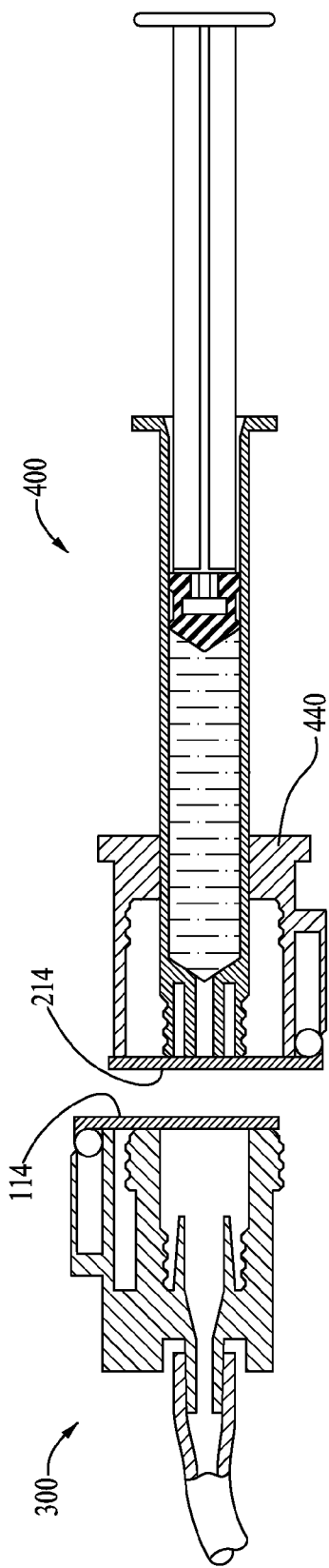
FIG. 4 shows a cut-away view of another embodiment of a sterile entry IV port and sterile entry syringe delivery mechanism.
Figure 5:
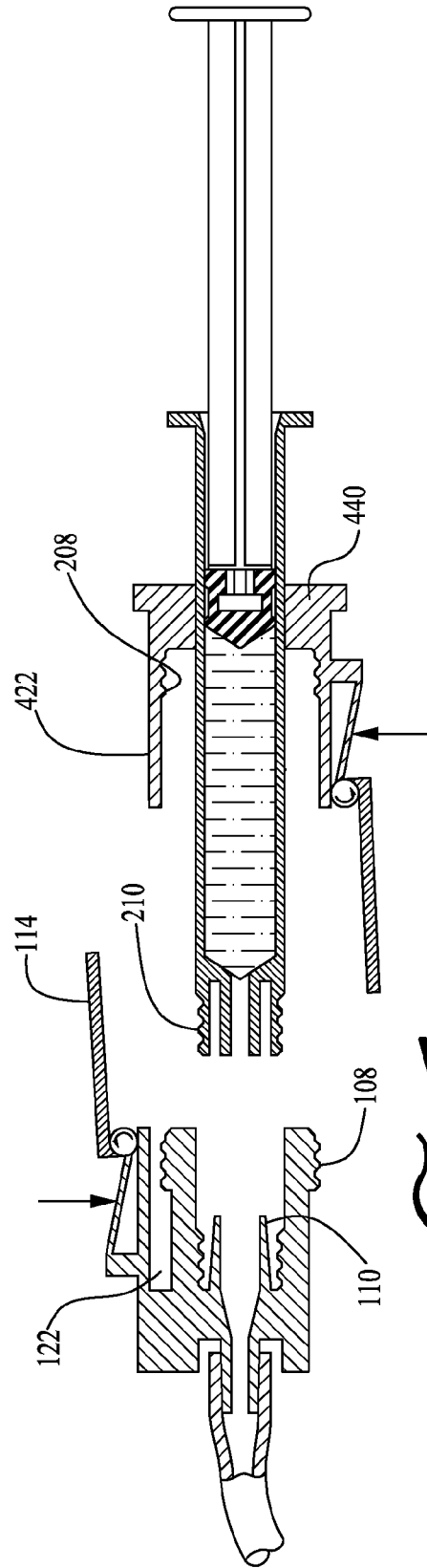
FIG. 5 shows a cut-away view of the sterile entry IV port and the sterile entry syringe delivery mechanism of FIG. 4 with the respective cover caps removed from the respective entry and exit points.
Figure 10:
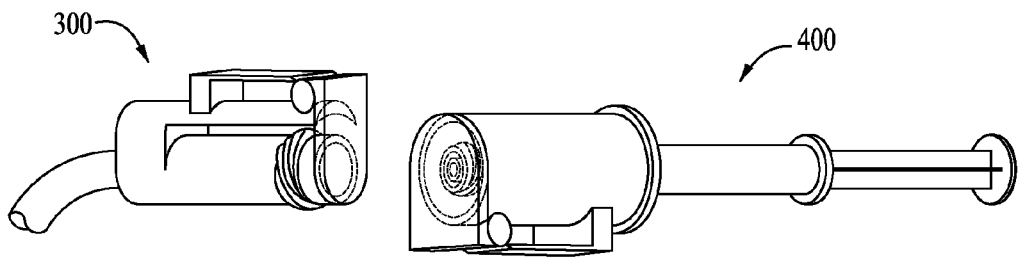
FIG. 10 is a perspective side view of the second embodiment as shown in FIG. 4.
Figure 11:
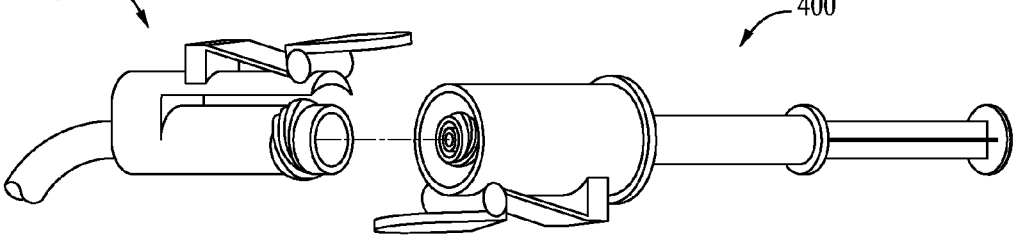
FIG. 11 is a perspective side view of the second embodiment as shown in FIG. 5.

FIG. 4 shows a cut-away view and FIG. 10 shows a perspective side view of the IV port 300 and the syringe mechanism 400 with the covers 114 and 214 in the closed position (referred to below as the "FIG. 4" embodiment and/or position). FIG. 5 shows a cut-away view and FIG. 11 shows a perspective side view of the IV port 300 and the syringe mechanism 400 with the covers 114 and 214 in the open position (referred to below as the "FIG. 4" embodiment and/or position). In the embodiments of FIGS. 4-7 and 10-11, the cover 214 can be part of a movable assembly 440. This assembly can slide or otherwise move; in the embodiment shown, the movable assembly can move to the position shown at 440'. Once the movable assembly 440 has been moved, the syringe mechanism 400 can be inserted into the IV port 300 such that the lock combination 110/210 can be locked, as shown in FIG. 6. The movable assembly 440 can then be slid or otherwise moved forward such that the portion 422 of the movable assembly 440 fits into the channel 122 of the IV port 100 and such that the lock combination 108/208 is made, as shown in FIG. 7. Once the IV port 300 and syringe mechanism 400 are appropriately secured as shown in FIG. 7, fluid delivery can commence as described above with regard to the embodiments of FIGS. 1-3.

Although the present invention has been described in detail with reference to certain preferred configurations thereof, other versions or combinations of the disclosed embodiments are possible. Therefore, the spirit and scope of the invention should not be limited to the versions described above.

I claim:

1. A sterile entry IV port for use with a syringe delivery mechanism, said IV port comprising:
   an IV port entry;
   a first portion of a hinge attached to an entry cap cover and a second portion of said hinge attached to said IV port adjacent to said IV port entry, said cap configured to cover said IV port entry when in a closed position;
   a mechanism to move said entry cap cover from said closed position to an open position in a non-contaminating manner to allow attachment of a fluid delivery device thereto, wherein said mechanism comprises a moveable push-surface, said moveable push surface having a first end longitudinally spaced from the IV port entry and attached to an exterior side wall of the IV port and a second end attached to said hinge such that pressing the moveable push surface causes the cap to move to the open position.

2. The sterile entry IV port of claim 1, wherein said entry cap cover is rotatable about said hinge in response to depression of said push surface.

3. The sterile entry IV port of claim 1, further comprising at least one luer lock fitting configured for mating with a fluid delivery device having a compatible lock fitting.

4. The sterile entry IV port of claim 1, further comprising at least two luer lock fittings, wherein each of said fittings is configured for mating with a fluid delivery mechanism having a compatible lock fitting.

5. A sterile entry syringe delivery mechanism for use with a sterile entry IV port, said syringe delivery mechanism, comprising:
   a syringe delivery tip;
   a first portion of a hinge attached to an entry cap cover and a second portion of said hinge attached to a point adjacent to the syringe delivery tip, said entry can cover configured to cover said syringe delivery tip when in a closed position;
   a mechanism to move said entry cap cover from said closed position to an open position to allow attachment of a fluid delivery device thereto, wherein said mechanism comprises a moveable push-surface, said hinge being located between the moveable push surface and the entry cap cover, said moveable push surface having a first end longitudinally spaced from the syringe delivery tip and attached to an exterior side wall of the syringe delivery tip and a second end attached to said hinge.

6. The sterile entry syringe delivery mechanism of claim 5, wherein said entry cap cover is rotatable about said hinge by applying pressure to the push surface.

7. The sterile entry syringe delivery mechanism of claim 5, further comprising at least one luer lock fitting configured for mating with a fluid entry port.

8. The sterile entry syringe delivery mechanism of claim 5, further comprising at least two luer lock fittings, wherein each of said fittings is configured for mating with a fluid entry port luer lock fitting.

* * * * *